US00PP33253P3

(12) United States Plant Patent
Larse

(10) Patent No.: US PP33,253 P3
(45) Date of Patent: Jul. 13, 2021

(54) STRAWBERRY PLANT NAMED 'STATA'

(50) Latin Name: ***Fragaria* x *ananassa***
Varietal Denomination: Stata

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 16/873,476

(22) Filed: Apr. 17, 2020

(65) Prior Publication Data

US 2020/0337193 P1 Oct. 22, 2020

Related U.S. Application Data

(60) Provisional application No. 62/835,705, filed on Apr. 18, 2019.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

(56) References Cited

U.S. PATENT DOCUMENTS

| | | | |
|---|---|---|---|
| PP7,614 | P | 8/1991 | Bringhurst et al. |
| PP29,966 | P2 | 12/2018 | Larse |
| 2020/0337191 | P1 | 10/2020 | Larse |
| 2020/0337192 | P1 | 10/2020 | Larse |

*Primary Examiner* — Susan McCormick Ewoldt
*Assistant Examiner* — Karen M Redden
(74) *Attorney, Agent, or Firm* — Cooley LLP

(57) ABSTRACT

The present invention provides a new and distinct strawberry variety designated as 'Stata' (a.k.a. '109740'). The 'Stata' cultivar is primarily adapted to growing conditions of the central coast of California and produces strong vigorous plants that remain in fruit production from March through October.

6 Drawing Sheets

Latin name of the genus and species: *Fragaria* x *ananassa.*

Varietal denomination: 'Stata'.

BACKGROUND OF THE INVENTION

The present invention relates to a new and distinct strawberry variety designated as 'Stata' (a.k.a. '109740').

'Stata' (a.k.a. '109740') is the result of a controlled-cross between a female parent cultivar designated '108999' (a proprietary cultivar made by the inventor, and not been made available to the public) and a male parent cultivar designated 'Preakness' (U.S. Plant Pat. No. 29,966). Following selection and during testing, the plant was originally designated '109740' and subsequently named 'Stata'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduce true to type in successive generations of asexual reproduction.

DESCRIPTION OF THE DRAWINGS

The accompanying color photographs depict various characteristics of the cultivar as nearly true as possible to make color reproductions. The age of the plants in FIGS. 1-6 is six months old.

SUMMARY OF THE INVENTION

Figure 1:
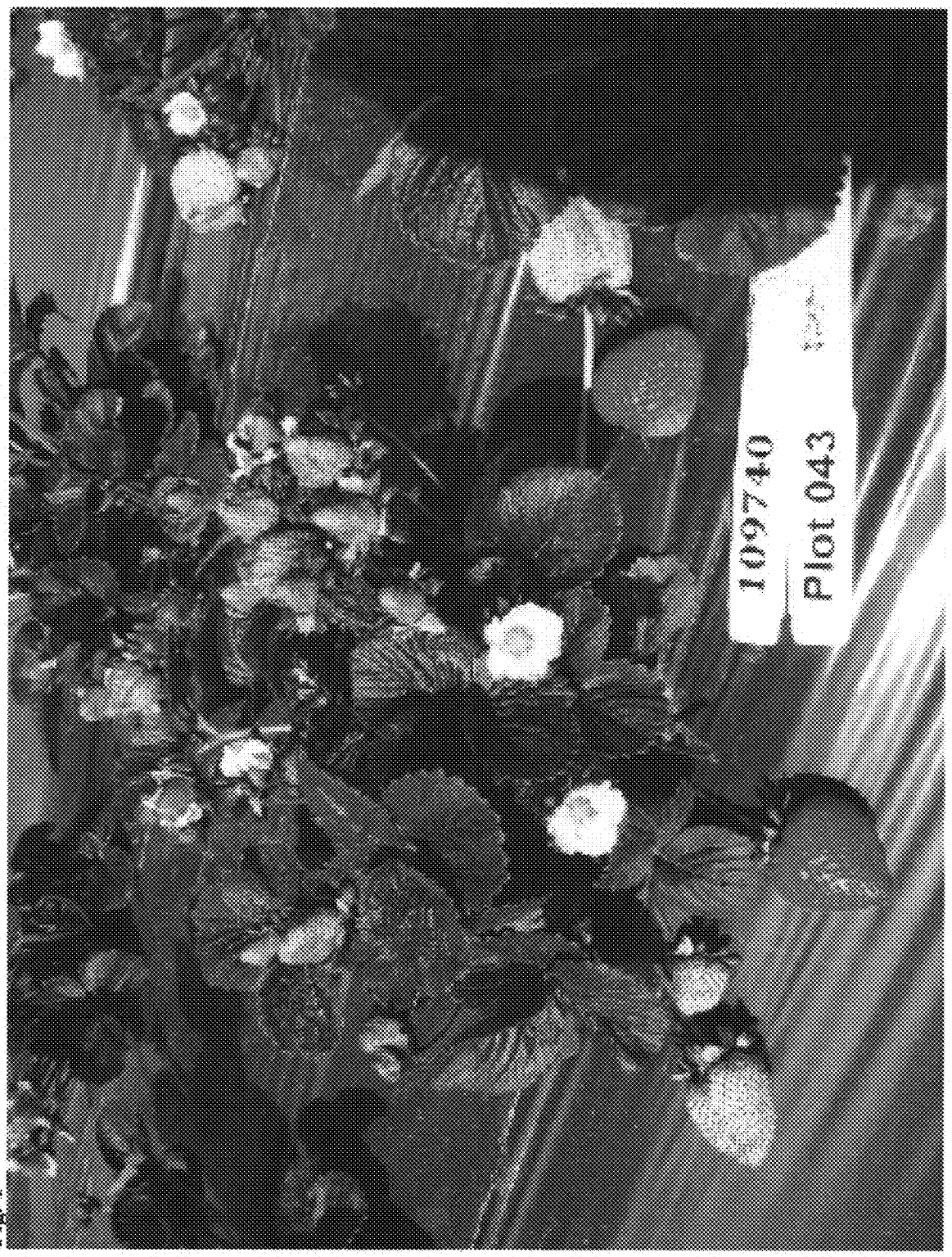
FIG. 1 shows 'Stata' plant with florescence and fruit.
Figure 2:
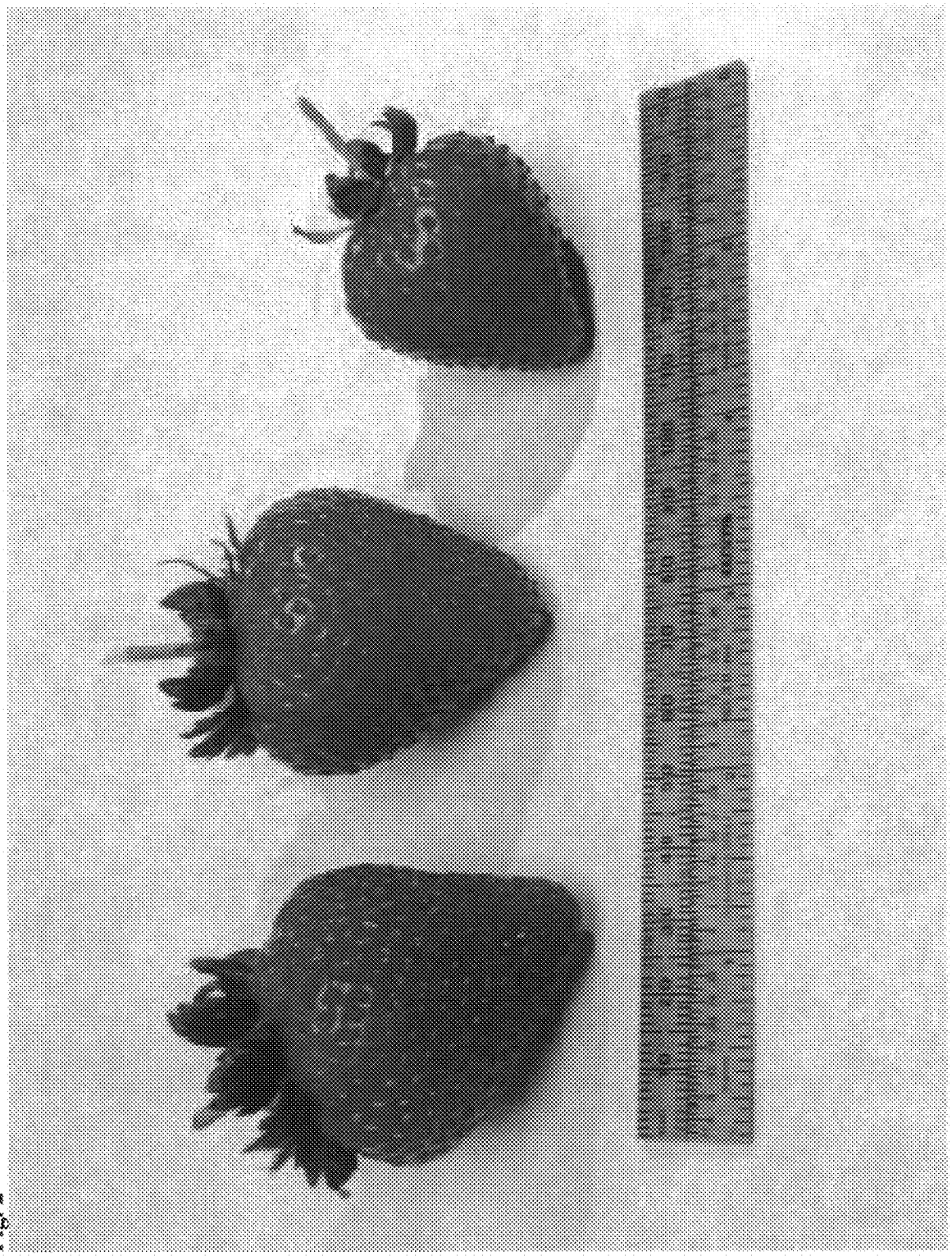
FIG. 2 shows 'Stata' fruit.
Figure 3:
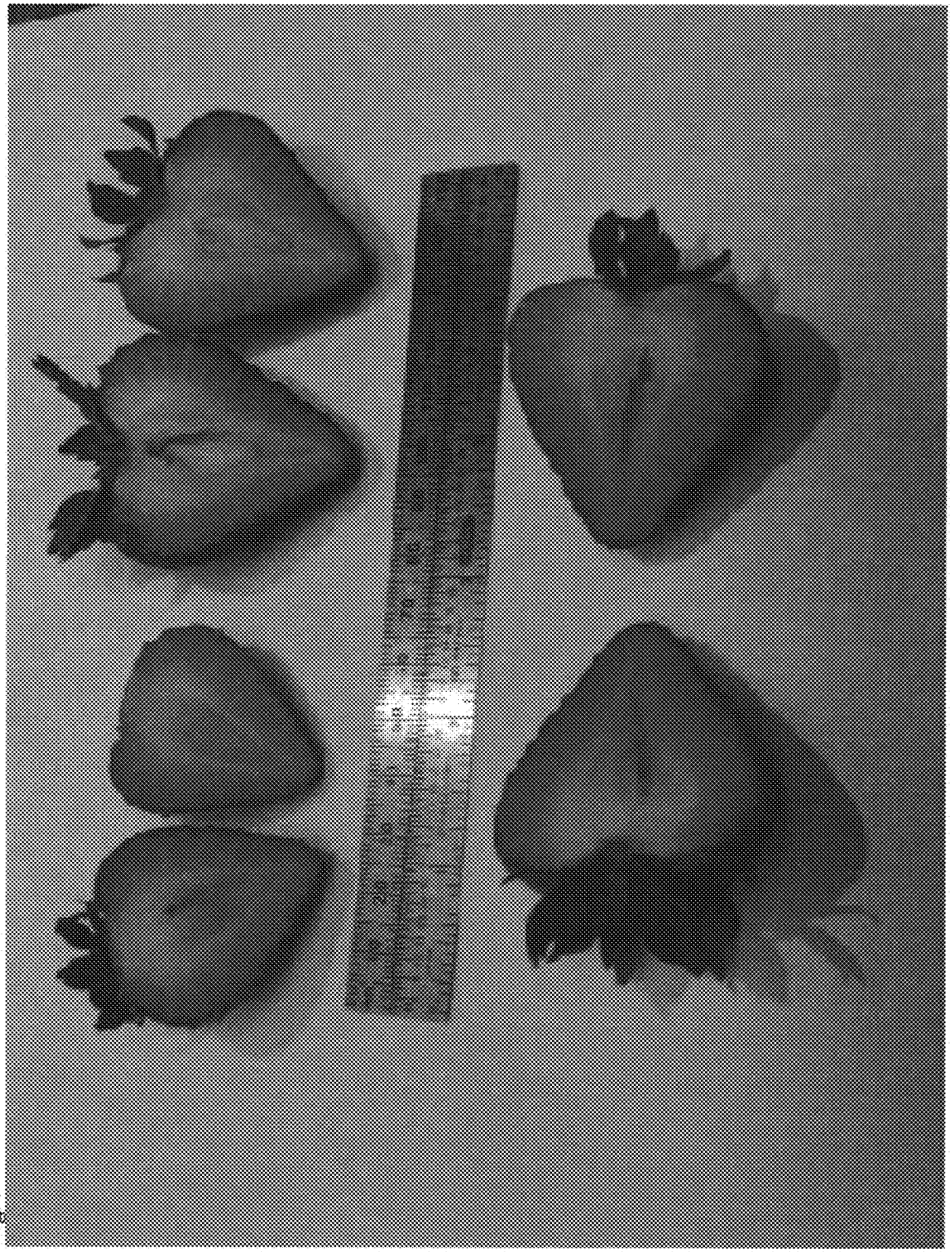
FIG. 3 shows 'Stata' fruit interior.
Figure 4:
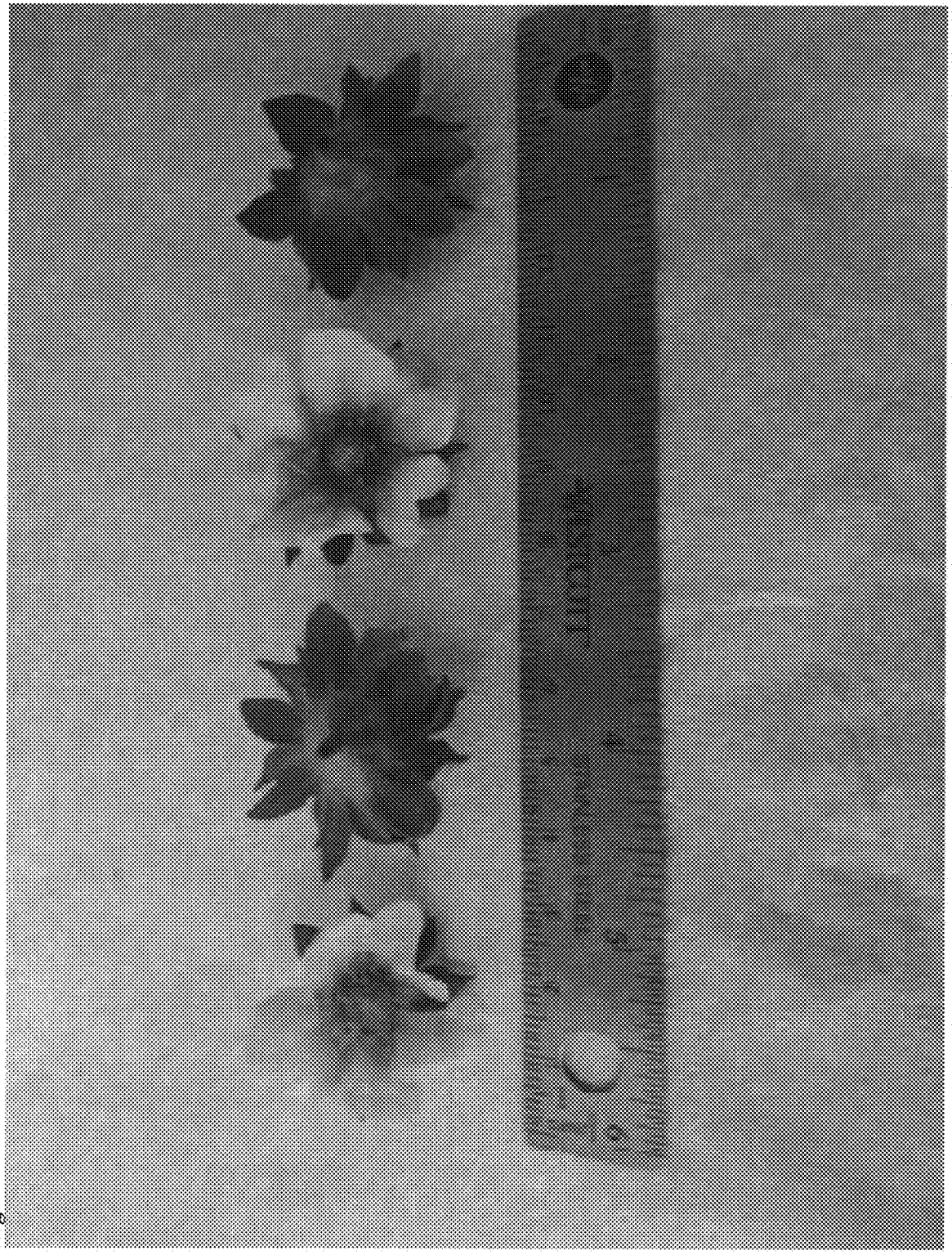
FIG. 4 shows 'Stata' flowers.
Figure 5:
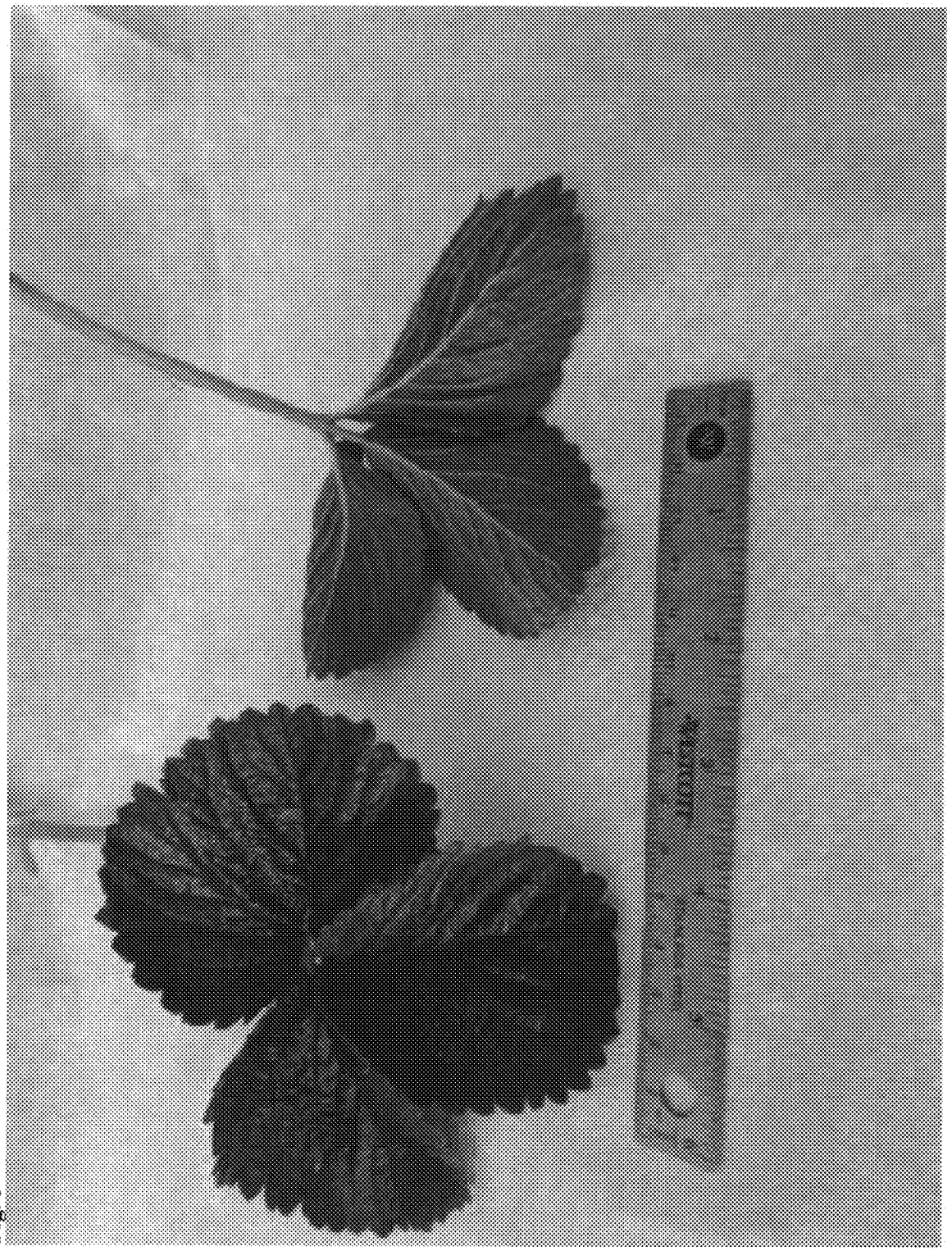
FIG. 5 shows 'Stata' leaf.
Figure 6:
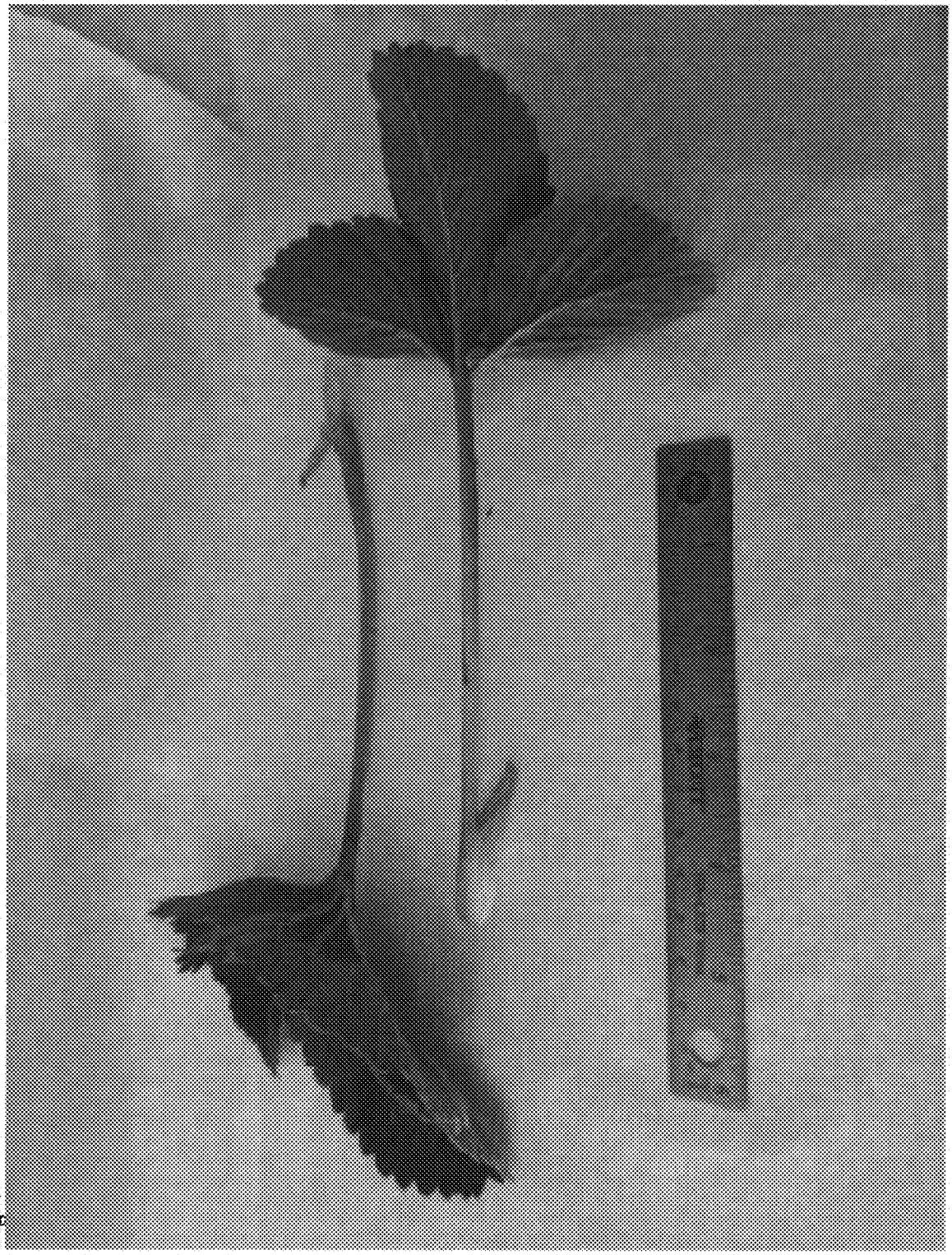
FIG. 6 shows 'Stata' petiole.

This invention relates to a new and distinctive strawberry cultivar designated as 'Stata' (a.k.a. '109740'). This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish the strawberry variety 'Stata' from known strawberry varieties. Plants for the botanical measurements in the present application were grown as annuals. Any color references are made to The Royal Horticultural Society Colour Chart, 1995 Edition, except where general terms of ordinary dictionary significance are used. The age of the plants in Table 1 is seven months old.

TABLE 1

Characteristics of Stata

| Characteristic Type | Characteristic | Stata |
|---|---|---|
| General | Plant Habit | annual |
| | Plant Growth Habit | upright |
| | Day length | neutral |
| | Planting season | Fall |
| | Height | 39.5 cm |
| | Width | 41.0 cm |
| | Density of foliage | light to medium |
| | Plant vigor | high |
| | Freezing Quality | moderate |
| | Rain/weather tolerance | moderate |
| | Harvest Ease | moderate |
| Leaf | Leaf Shape | concave |
| | Leaflet texture | soft |
| | Leaf average width | 127 mm |
| | Leaf average length | 83 mm |
| | Terminal leaflet width | 76 mm |
| | Terminal leaflet length | 81 mm |
| | Terminal leaflet length/width ratio | 1.07 |
| | Teeth per terminal leaflet | 18 to 25 |
| | Shape of the terminal leaflet base | rounded to acute |
| | Shape of terminal leaflet in cross-section | concave |
| | Shape of the terminal leaflet margin | serrate to crenate |
| | Color of upper side of leaflet | RHS 137A |
| | Color of lower side of leaflet | RHS 139C |
| | Leaf blistering | weak |
| | Leaf glossiness | medium |
| | Leaf variegation | absent |
| | Number of leaflets per leaf | 3 |
| | Terminal Leaflet margin | flat |
| | Terminal Leaflet shape | orbicular |
| | Terminal Leaflet shape of apex | rounded |
| Limbs | Petiole length | 25 cm |
| | Petiole diameter | 3.65 mm |
| | Petiole pubescence | dense |
| | Petiole pose of hairs | horizontal |
| | Petiole color | RHS 145A |
| | Petiolule length | 1.3 cm |
| | Petiolule diameter | 2.60 mm |
| | Petiolule color | RHS 145A |
| | Stipule length | 3.1 cm |
| | Stipule width | 0.6 cm |
| | Stipule pubescence | medium |
| | Stipule anthocyanin | present |
| | Stipule color (color code) | RHS 145C |
| | Pedicel average length | 19.8 cm |
| | Pedicel average diameter | 3.12 mm |
| | Pedicel color (color code) | RHS 144A |
| | Attitude of hairs on peduncle and pedicel | horizontal |
| | Peduncle average length | 25.8 mm |
| | Peduncle average diameter | 3.4 mm |
| Inflore-scence | Inflorescence position relative to foliage | above |
| | Flower arrangement of petals | touching |
| | Flower size | medium to large |
| | Flower diameter | 2.6 cm |
| | Petal shape | orbicular |
| | Petal apex | rounded |
| | Petal margin | entire |
| | Petal base shape | concave |
| | Petal length | 1.6 cm |
| | Petal width | 1.6 cm |
| | Petal length/width ratio | 1 |
| | Petal number per flower | 5 to 7 |
| | Number of flowers | 41 to 61 |
| | Upper Petal color | RHS 155C |
| | Lower Petal color | RHS 155C |
| | Peduncle size | medium |
| | Floral Calyx Diameter | 3.0 cm |
| | Corolla diameter | 2.6 cm |
| | Calyx diameter relative to corolla | equal to larger |
| | Inner calyx diameter relative to outer | equal |

TABLE 1-continued

Characteristics of Stata

| Characteristic Type | Characteristic | Stata |
|---|---|---|
| | Sepal shape | elliptical |
| | Sepal apex | convex |
| | Sepal margin | entire |
| | Sepal length | 0.7 to 1.3 cm |
| | Sepal width | 0.2 to 0.6 cm |
| | Sepal number per flower | 10 to 14 |
| | Sepal color (upper) | RHS 137C |
| | Sepal color (lower) | RHS 147C |
| | Receptacle color | RHS 145A |
| | Fertility | not-tested |
| | Time of flowering (50% of plants in bloom) | April to May |
| | Shape of stigma | capitate |
| | Color of stigma | RHS 163B |
| | Length of style | 1.4 to 2.0 mm |
| | Color of style | RHS 4A |
| | Color of the ovary | 150B |
| | Number of stamen | 24 to 30 |
| | Length of the stamens | 2.0 to 6.0 mm |
| | Shape of anther | dorsifixed |
| | Size of anther | 1.0 to 1.5 mm |
| | Color of anther | RHS 163B |
| | Amount of pollen | moderate |
| | Color of pollen | RHS 13B to RHS 163B |
| | Color of filament | RHS 2D |
| | Length of filament | 1.0 to 5.0 mm |
| Stolon | Stolon number | 1 to 3 |
| | Stolon anthocyanin | RHS 183A |
| | Stolon thickness | medium |
| | Stolon pubescence | sparse |
| | Widest diameter of stolon at leaf attachment | 3.17 mm |
| | Stolon average length | 44.9 cm |
| | Stolon color | RHS 145A |
| Fruit | Fruiting truss length | 11.5 to 17.0 cm |
| | Fruiting truss diameter | 3.38 mm |
| | Number of fruit per truss | 3 to 8 |
| | Truss color | 144A |
| | Fruit length | 43 to 53 cm |
| | Fruit width | 41.5 cm |
| | Fruit skin color | RHS 45A |
| | Fruit flesh color excluding core | RHS 44A |
| | Fruit core color | RHS 39B |
| | Fruit length/width ratio | 1.04 to 1.28 |
| | Fruit weight | 25.6 g |
| | Relative fruit size | medium |
| | Predominant fruit shape | globose-conic to conic |
| | Shape difference between primary & second | No shape difference |
| | Width of band without of achenes | narrow |
| | Fruit glossiness | medium to strong |
| | Position of achenes | even |
| | Achene color | RHS 135C |
| | Achenes per fruit | 261 |
| | Achene weight | 0.157 g |
| | Position of calyx | below surface |
| | Fruit Calyx Diameter | 4.5 cm |
| | level of adherence of calyx | strong |
| | Color of calyx | RHS 137A |
| | Pose of calyx segments | reflexed |
| | of calyx in relation to fruit | smaller |
| | Firmness of flesh | firm |
| | Evenness of flesh color | even |
| | Fruit hollow length | 2.6 cm |
| | Fruit hollow width | 1.0 cm |
| | Fruit hollow length/width ratio | 2.6 |
| | Hollow center | medium |
| | Sweetness | 8 Brix |
| | Acidity | 3.18 |
| | Texture when tasted | fine |

TABLE 1-continued

| Characteristics of Stata | | |
|---|---|---|
| Characteristic Type | Characteristic | Stata |
| | Time of flowering | May |
| | Time of fruit ripening | May |
| | Harvest maturity (50% of plants with ripe fruit) | June |
| | Type of bearing | day neutral |
| | Grams of fruit per plant | 698 g |
| | Yield (lb per acre) | 30,777 lb/acre |
| | Firmness | firm to very firm |
| | Surface Texture | smooth |
| | Fruit Appearance (1-7 scale; 7 = best) | 6 |
| | Storage longevity | 5 to 10 days |
| Horti-cultural | Crop suitability | Fresh market |
| | Temperature tolerance range | −1° C. to 36° C. |
| | USDA Hardiness Zone adaptability for annual transplanting of California grown commercial rootstock | 6a,6b,7a,7b,8a, 8b,9a,9b |
| | Cull rate (% Usable) | 13.6% |

'Seascape' (U.S. Plant Pat. No. 7,614) is a commercial strawberry variety that is similar to, but distinguished from 'Stata'. The plant of the new strawberry plant variety 'Stata' is smaller compared to 'Seascape'. The florescence of 'Stata' extend beyond the canopy of the plant and the ripe fruit is visible making 'Stata' easier to harvest compared to the hand harvest of the fruit of 'Seascape', some of which ripens beneath the canopy of the plant. The full season Yield of fruit from the new strawberry plant variety 'Stata' is greater than the fruit Yield of comparison variety 'Seascape' and the percentage of marketable fruit from new variety 'Stata' is greater than the percent of marketable fruit of 'Seascape'. The average weight of the fruit of 'Stata' is slightly less than the average weight of the fruit of 'Seascape'. The fruit of 'Stata' is firmer than the fruit of 'Seascape'. The color of the fruit of 'Seascape' is deeper red than the fruit color of 'Stata'.

The florescence of 'Stata' extends beyond the plant canopy and is different compared to female parent '108999' with florescence that is about even with the canopy. The overall volumetric plant shape of the 'Stata' plant is described as round and is different in comparison to the oblate spreading shape of the female parent plant '108999'. The fruit of 'Stata' is less firm compared to the fruit of female parent '108999'. The conical shape of the fruit of 'Stata' differs from female parent '108999'. The ratio of the height of the fruit of 'Stata' and the width of the fruit of 'Stata' is very near unity and the dimensional ratio of height to width of female parent '108999' is greater than unity. The fruit Yield of 'Stata' is similar to its female parent '108999', but the percentage of marketable fruit from 'Stata' is greater than the percentage of marketable fruit produced by female parent '108999'. Compared to its male parent the yield of marketable fruit Yield of 'Stata' is less than the marketable fruit yield of male parent 'Preakness'. The fruit of 'Stata' is firmer than the fruit of male parent 'Preakness'. The size of the 'Stata' plant is larger than size of its male parent plant 'Preakness'.

The invention claimed is:

1. A new and distinct cultivar of strawberry plant named 'Stata' substantially as shown and described herein.

* * * * *